United States Patent
Baccelli

(10) Patent No.: US 8,882,808 B2
(45) Date of Patent: *Nov. 11, 2014

(54) SPINAL IMPLANT

(75) Inventor: Christian Baccelli, Saucats (FR)

(73) Assignee: Zimmer Spine S.A.S., Bordeaux (FR)

( * ) Notice: Subject to any disclaimer, the term of this patent is extended or adjusted under 35 U.S.C. 154(b) by 357 days.

This patent is subject to a terminal disclaimer.

(21) Appl. No.: 13/040,404

(22) Filed: Mar. 4, 2011

(65) Prior Publication Data

US 2011/0152950 A1      Jun. 23, 2011

Related U.S. Application Data

(63) Continuation of application No. 10/569,607, filed as application No. PCT/FR2004/002249 on Sep. 3, 2004, now Pat. No. 7,901,436.

(30) Foreign Application Priority Data

Sep. 4, 2003   (FR) ...................................... 03 10480

(51) Int. Cl.
   *A61B 17/70*         (2006.01)
(52) U.S. Cl.
   CPC .................................. *A61B 17/7032* (2013.01)
   USPC .......................................... 606/267; 606/279
(58) Field of Classification Search
   USPC .......................................... 606/246, 264–279
   See application file for complete search history.

(56) References Cited

U.S. PATENT DOCUMENTS

| | | |
|---|---|---|
| 255,428 A | 3/1882 | Graham |
| 4,946,458 A | 8/1990 | Harms et al. |
| 4,950,269 A | 8/1990 | Gaines |
| 5,010,879 A | 4/1991 | Moriya et al. |
| 5,147,359 A | 9/1992 | Cozad et al. |

(Continued)

FOREIGN PATENT DOCUMENTS

| | | |
|---|---|---|
| DE | 3032237 A1 | 3/1982 |
| DE | 3916198 | 11/1990 |

(Continued)

OTHER PUBLICATIONS

Strong, Simple and Low Profile, Ovation Polyaxial System, by Osteotech, Inc., Eatontown, NJ, 6 pages, at www.osteotech.com, 2011.

(Continued)

*Primary Examiner* — Kevin T Truong
*Assistant Examiner* — Michael Araj
(74) *Attorney, Agent, or Firm* — Seager, Tufte & Wickhem, LLC

(57) ABSTRACT

This disclosure relates to a spinal implant that can provisionally retain a rod in an assembly head without having to first lock the rod relative to the assembly head. The spinal implant has a clip insert structured to retain the rod in the assembly head. The clip insert has a top portion with a cylindrical opening and extending over the cylindrical opening to cover the connection rod in part when the connection rod is engaged in the clip insert. The top portion is deformable by application of force on the connection rod to engage the connection rod with the clip insert. The clip insert and the assembly head are mechanically decoupled and can be fully received within the assembly head. The mechanical forces to which the assembly head is subjected are not transmitted to the clip insert.

20 Claims, 3 Drawing Sheets

(56) References Cited

U.S. PATENT DOCUMENTS

| | | | |
|---|---|---|---|
| 5,181,917 | A | 1/1993 | Rogozinski |
| 5,201,734 | A | 4/1993 | Cozad et al. |
| 5,207,678 | A | 5/1993 | Harms et al. |
| 5,346,493 | A * | 9/1994 | Stahurski et al. ............ 606/300 |
| 5,380,324 | A | 1/1995 | Muller |
| 5,385,583 | A | 1/1995 | Cotrel |
| 5,437,669 | A | 8/1995 | Yuan et al. |
| 5,443,467 | A * | 8/1995 | Biedermann et al. ........... 606/65 |
| 5,536,268 | A | 7/1996 | Griss |
| 5,545,165 | A | 8/1996 | Biedermann et al. |
| 5,562,663 | A | 10/1996 | Wisnewski et al. |
| 5,628,740 | A | 5/1997 | Mullane |
| 5,630,817 | A | 5/1997 | Steib |
| 5,672,176 | A | 9/1997 | Biedermann et al. |
| 5,683,392 | A | 11/1997 | Richelsoph et al. |
| 5,690,630 | A | 11/1997 | Errico et al. |
| 5,725,527 | A | 3/1998 | Biedermann et al. |
| 5,728,098 | A | 3/1998 | Sherman et al. |
| 5,733,286 | A | 3/1998 | Errico et al. |
| 5,782,833 | A | 7/1998 | Haider |
| 5,876,459 | A | 3/1999 | Powell |
| 5,879,350 | A | 3/1999 | Sherman et al. |
| 5,885,286 | A * | 3/1999 | Sherman et al. ............ 606/270 |
| 5,964,760 | A * | 10/1999 | Richelsoph ................. 606/279 |
| 6,010,503 | A | 1/2000 | Richelsoph et al. |
| 6,050,997 | A | 4/2000 | Mullane |
| 6,053,917 | A * | 4/2000 | Sherman et al. ............ 606/270 |
| 6,090,111 | A * | 7/2000 | Nichols ................... 606/266 |
| 6,162,234 | A | 12/2000 | Freedland et al. |
| 6,273,888 | B1 | 8/2001 | Justis |
| 6,302,882 | B1 | 10/2001 | Lin et al. |
| 6,331,179 | B1 | 12/2001 | Freid et al. |
| 6,371,957 | B1 | 4/2002 | Amrein et al. |
| 6,451,021 | B1 | 9/2002 | Ralph et al. |
| 6,457,789 | B2 | 10/2002 | Hallstein |
| 6,485,492 | B1 | 11/2002 | Halm et al. |
| 6,485,494 | B1 | 11/2002 | Haider |
| 6,547,789 | B1 | 4/2003 | Ventre et al. |
| 6,554,834 | B1 | 4/2003 | Crozet et al. |
| 6,565,565 | B1 | 5/2003 | Yuan et al. |
| 6,613,050 | B1 | 9/2003 | Wagner et al. |
| 6,626,908 | B2 | 9/2003 | Cooper |
| 6,755,829 | B1 | 6/2004 | Bono et al. |
| 7,087,057 | B2 | 8/2006 | Konieczynski et al. |
| 7,141,051 | B2 | 11/2006 | Janowski et al. |
| 7,335,201 | B2 | 2/2008 | Doubler et al. |
| 7,901,436 | B2 | 3/2011 | Baccelli |
| 2001/0001119 | A1 | 5/2001 | Lombardo |
| 2001/0053913 | A1 | 12/2001 | Freedland et al. |
| 2002/0052603 | A1 | 5/2002 | Nichols et al. |
| 2002/0082602 | A1 | 6/2002 | Biedermann et al. |
| 2002/0133154 | A1 | 9/2002 | Saint Martin |
| 2003/0125742 | A1 | 7/2003 | Yuan et al. |
| 2003/0199873 | A1 | 10/2003 | Richelsoph |
| 2004/0186474 | A1 | 9/2004 | Matthis et al. |
| 2005/0277927 | A1 | 12/2005 | Guenther et al. |

FOREIGN PATENT DOCUMENTS

| | | |
|---|---|---|
| DE | 10256095 | 12/2002 |
| EP | 0536066 | 4/1993 |
| EP | 1064885 A | 1/2001 |
| FR | 2151475 | 4/1973 |
| FR | 2720923 | 12/1995 |
| FR | 2780269 A | 12/1999 |
| WO | WO9203100 | 3/1992 |
| WO | WO9501132 | 1/1995 |
| WO | WO9621396 | 7/1996 |
| WO | WO03058086 A1 | 8/2003 |
| WO | WO2004103194 | 12/2004 |
| WO | WO2005122930 A2 | 12/2005 |

OTHER PUBLICATIONS

Paragon Posterior Spinal System, Danek Medical, Inc. catalog, Memphis, TN, 1993, 5 pages.

Spiral Radius 90D System Overview, Surgical Dynamics Inc. catalog, Feb. 26, 2001, 10 pages.

Ovation Polyaxial System, Osteotech, Inc. online catalog, 2003 at www.osteotech.com, printed Jan. 2004, 16 pages.

Translation of France Application FR 2780269 entitled Spinal Implant by Senegas filed Dec. 31, 1999, from United States Patent and Trademark Office, Mar. 2008, 17 pages.

International Search Report from PCT/US2005/020886 dated Feb. 22, 2006, 6 pages.

International Preliminary Examination Report and Written Opinion dated Apr. 10, 2002, in PCT/US2005/020886, dated Dec. 14, 2006, 15 pages.

International Preliminary Report on Patentability, International Application No. PCT/FR2004/002249, mailed Mar. 6, 2006, 6 pages.

International Preliminary Report on Patentability with English translation, International Application No. PCT/FR2004/002249, mailed Mar. 6, 2006, 7 pages.

Examination Report, European Patent Application No. EP 04787304.7, mailed Feb. 2, 2009, 4 pages.

International Search Report Application No. PCT/FR2004/002249, mailed Feb. 18, 2005, 6 pages.

Office Action issued in U.S. Appl. No. 10/569,607, mailed Jul. 17, 2007, 5 pages.

Office Action issued in U.S. Appl. No. 10/569,607, mailed Feb. 26, 2008, 5 pages.

Office Action issued in U.S. Appl. No. 10/569,607 mailed Nov. 14, 2008, 5 pages.

Office Action issued in U.S. Appl. No. 10/569,607 mailed Jun. 1, 2009, 6 pages.

Office Action issued in U.S. Appl. No. 10/569,607 mailed Nov. 25, 2009, 7 pages.

Examination Report issued in Australian Patent Application No. AU 2004269942 mailed May 11, 2009, 2 pages.

French Search Report, issued in French Patent Application No. 0310480, dated Apr. 15, 2004, 2 pages.

French Search Report, issued in French Patent Application No. 9808128, dated Mar. 3, 1999, 1 page.

Office Action issued in U.S. Appl. No. 10/569,607 mailed Apr. 27, 2010, 9 pages.

Notice of Allowance in U.S. Appl. No. 10/569,607, mailed Nov. 23, 2010, 7 pages.

* cited by examiner

SPINAL IMPLANT

CROSS-REFERENCE TO RELATED APPLICATIONS

This application is a continuation of U.S. patent application Ser. No. 10/569,607, filed Nov. 3, 2006 now U.S. Pat. No. 7,901,436, entitled "Spinal Implant," which is a national phase filing of PCT Application No. PCT/FR2004/002249, filed Sep. 3, 2004, which claims priority to French Patent Application No. 0310480, filed Sep. 4, 2003, all of which are hereby fully incorporated by reference herein.

TECHNICAL FIELD

The invention relates to an implant for spinal surgery and, more particularly, it relates to devices for osteosynthesis and for arthrodesis.

SUMMARY

In the invention, the spinal implant comprises, at a first end, fastener means for fastening to a vertebra, and at a second end, an assembly head extending along an axis x-x', said head including a housing that is open away from the fastener means and that presents a section that is substantially U-shaped, said head being suitable for receiving a connection rod extending transversely to the axis x-x' and for securing it by clip retention means and by locking means.

Such an implant is already known, e.g. from document FR 2 780 269. It relates to a spinal implant of the above-specified type having clip retention means in the form of a protuberance situated in the housing and extending towards the inside thereof. In order to be retained, the connection rod is clipped into the bottom portion of the housing by using the protuberance.

Thereafter, the rod is locked by an external ring that is screwed onto the assembly head. The function of the external ring is to clamp together the side branches of the assembly head, or at least to ensure that they do not splay apart. To do this, the inside diameter of the ring is substantially equal to the outside diameter of the assembly head, so as to be capable of sliding on the assembly head and thus of pressing closely against its side branches.

That outer ring is essential for ensuring that the rod is locked in place. Without that ring, the branches could splay apart because of the force applied to insert the rod in the clip retention means, in particular after the implant has been used on numerous occasions. As a result, the rod would be no longer held sufficiently securely in the housing and could therefore separate from the implant.

The use of an outer ring for the locking means considerably increases the overall dimensions of the implant and obliges the surgeon carrying out the surgery to provide sufficient space in advance around the implant in order to allow the external ring to be put into place.

Another drawback appears when putting the outer ring into place, and more generally when putting any element into place that is to be screwed onto the outside surface of the assembly head of such an implant.

During this locking operation when using an outer ring, it is possible that tissue, veins or nerves, can become entrained by the turning ring or can be pinched between the ring and the assembly head. In addition, in the mounted position, the external parts or threads present sharp edges that could cut through tissue situated close to the implant. It will readily be understood that it is desirable, whenever possible, to avoid damaging human tissue.

Another drawback of previously known implants lies in the fact that the surgeon must constantly hold the rod in place while its position is being adjusted, or indeed until the assembly head has been locked.

The invention seeks to remedy those drawbacks.

This object is achieved by the facts that, in the assembled position, the clip retention means and the locking means are fully received within the assembly head, and that the clip retention means (40) are mechanically decoupled from the locking means (50).

The term "clip retention means" designates means serving to prevent the rod becoming disassembled easily, while still leaving it free to turn about its own axis and to move in translation lengthwise.

The term "locking means" is used to designate means that prevent any movement of the rod relative to the assembly head.

The clip retention means are suitable for holding the connection rod in the assembly head on their own; in other words, the retention means can perform their function in the absence of the locking means, or even before the assembly head is locked.

It will be understood that that spares the surgeon of any need to hold the connection rod while adjusting the position of the implant or of the rod, and/or while locking the assembly head.

In addition, all of the means required for securing the connection rod are contained within the assembly head. No element is screwed or inserted on the outside surface of the assembly head, so there is no risk damaging tissue or veins in the vicinity of the implant.

Advantageously, the clip retention means are constituted by a part that is separate and that can be separated from the assembly head.

Thus, it is possible to change the clip retention means so as to adapt to the diameter of the connection rod that is to be used. This change could also be necessary if, after several uses, the clip retention means no longer perform their function.

Advantageously, the locking means comprise a locknut suitable for being screwed into internal tapping of the assembly head.

Thus, in the assembled position, the locknut is received in full inside the assembly head.

BRIEF DESCRIPTION OF THE DRAWINGS

The invention can be better understood and its advantages can be seen better on reading the following detailed description of embodiments given as non-limiting examples. The description refers to the accompanying drawings, in which.

DETAILED DESCRIPTION

Figure 1:
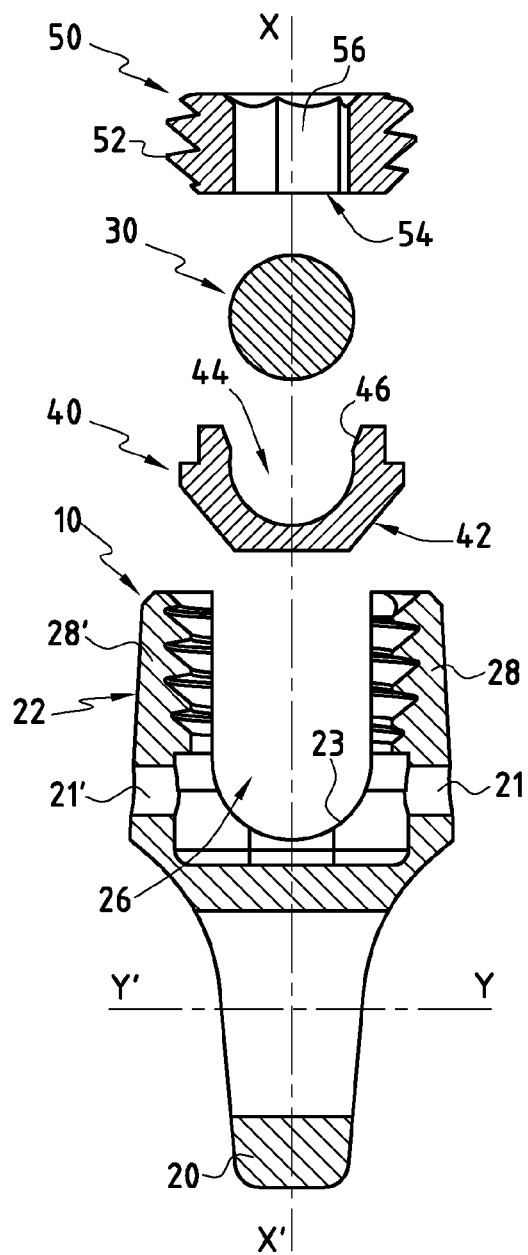
FIG. 1 is a face view in exploded section showing the various components of the spinal implant and the connection rod.

FIG. 1 shows the spinal implant in a face view and in section.

As can be seen in this figure, the spinal implant 10 has, at its first end, fastener means 20 in the form of a hook. The hook is used or securing the spinal implant to a process of a vertebra (not shown herein).

The second end of the implant comprises an assembly head 22 suitable for securing connection rods 30. Such rods serve to correct the orientation of the spinal column of a patient suffering from scoliosis, for example.

The implant shown herein has transverse and longitudinal dimensions lying in the range 5 millimeters (mm) to 20 mm. The connection rod 30 may have a variety of diameters, preferably lying in the range 5 mm to 6 mm.

The assembly head 22 of the spinal implant presents an outside shape that is substantially cylindrical about the axis x-x'. It possesses internal tapping 24 and has two side openings 26, 26', which between them define two side walls 28, 28'.

As can be seen in FIG. 1, the section of the assembly head in a plane (XOY) orthogonal to the plane of symmetry of the implant, is substantially U-shaped, and the bottom portions of the openings present semicylindrical profiles 23 for supporting the outside surface of the connection rod 30.

The internal tapping 24 of the assembly head 22 is of the "artillery" type, i.e. it presents an asymmetric trapezoidal thread. The advantage of this type of thread is that it enables the radial component of the screw-fastening force to be reduced. The advantage of this is explained in greater detail below.

The assembly head 22 further includes two orifices 21, 21' situated in the side walls 28, 28'. During the surgical operation, the surgeon uses an instrument for putting the implant into place. At one of its ends, the instrument has two studs that are received in the orifices 21, 21' in order to hold the implant.

Once the surgeon has determined the type of connection rod 30 that is to be used, clip retention means 40 are placed in the assembly head 22 to retain the connection rod in the assembly head before it is locked. The known advantage is to avoid any need for the surgeon to hold the connection rod while adjusting the position of the rod and while locking it. While position is being adjusted, the rod can move in translation in the retention means 40 and can also pivot about its own axis. However, the retention means 40 prevents the rod from escaping from the assembly head 22.

The retention means is in the form of a clip insert 40. Several types of insert are available corresponding to rods 30 of different diameters.

All these various inserts can be fitted in the same assembly head 22.

The insert is in the form of a cylindrical part of diameter slightly smaller than the inside diameter of the opening in the assembly head, and on its bottom portion it carries a thread 42 to enable it to be secured to the head by being turned through one-fourth of a turn.

In its top portion, it presents an open cylindrical opening 44 of diameter substantially equal to the diameter of the connection rod, and extending over slightly less than 180° so as to cover the connection rod in part when it is engaged in the insert. It will be understood that this engagement is achieved by applying a small amount of force on the connection rod so as to deform the top 46 of its cap-shape temporarily. This forced engagement clips the connection rod into the insert 40.

Once the rod 30 is properly in position, the surgeon can proceed to lock it in position.

Figure 2:
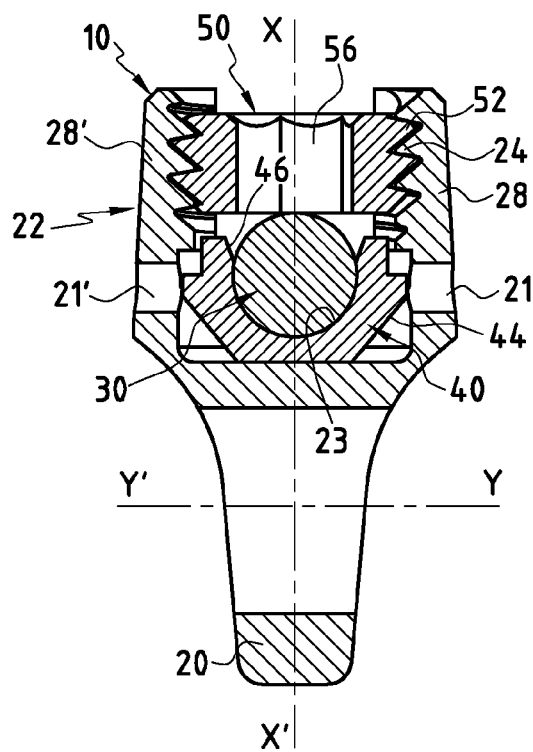
FIG. 2 is a face view in section, in the assembled position, showing the spinal implant and the connection rod.
Figure 3:
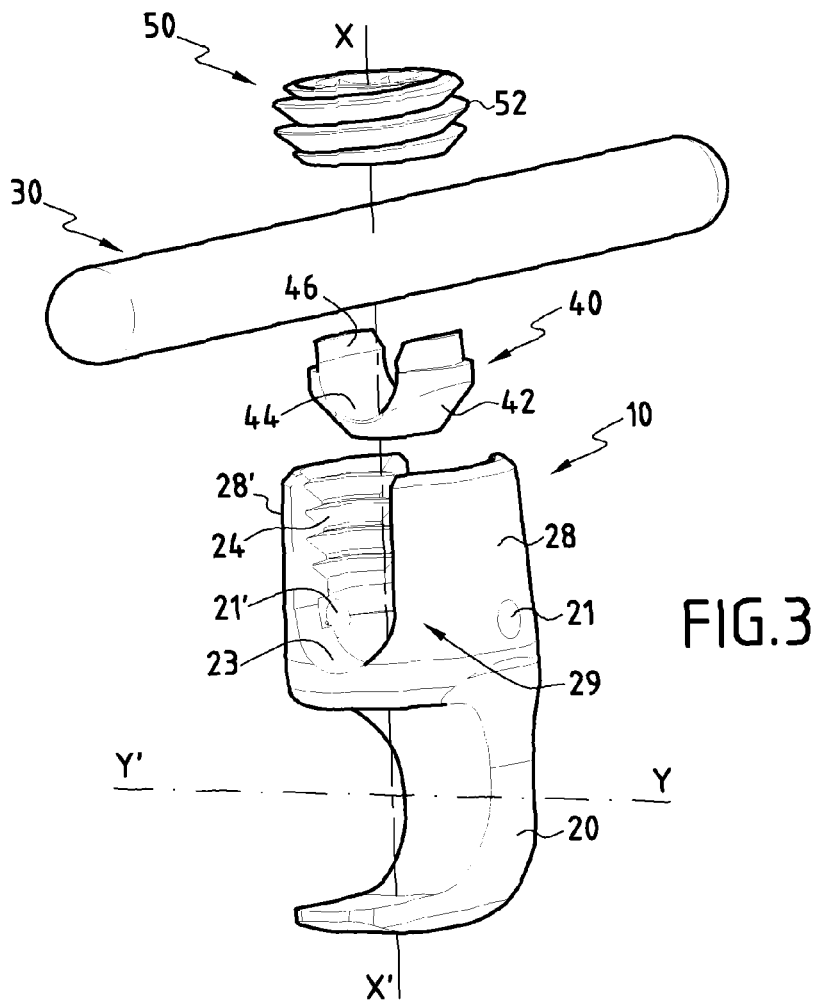
FIG. 3 is an exploded view in perspective showing the various components of the spinal implant and of the connection rod.

The locking means have inside tapping 24 as mentioned above and a locknut 50 that is to be screwed into the tapping 24. As can be seen in FIGS. 1 and 2, the locknut is cylindrical in shape and possesses an "artillery" type thread 52 suitable for co-operating with the tapping 24 of the assembly head 22.

When the locknut 50 is screwed into the assembly head 22, its bottom portion 54 comes into contact with the outside surface of the rod so as to secure the rod to the implant. The top portion of the locknut includes, in conventional manner, a hexagonal socket 56 suitable for receiving a tightening tool (not shown herein).

The use of a thread of the "artillery" type presents the advantage of reducing radial force while tightening the locknut. As a result, the side walls 28, 28' are no longer subjected to a radial force tending to splay them apart from each other. By using this type of tapping, there is no longer any need to use an external hooping ring for holding the walls at the desired spacing.

In any event, even if there is any residual force tending to space the walls 28, 28' apart, the insert 40 would continue to hold the rod 30, since the insert and the assembly head are mechanically decoupled, i.e. the mechanical forces to which the assembly head 22 is subjected are not transmitted to the insert 40.

It will thus be understood that it is entirely pointless using an external hooping ring with this device.

Figure 4:
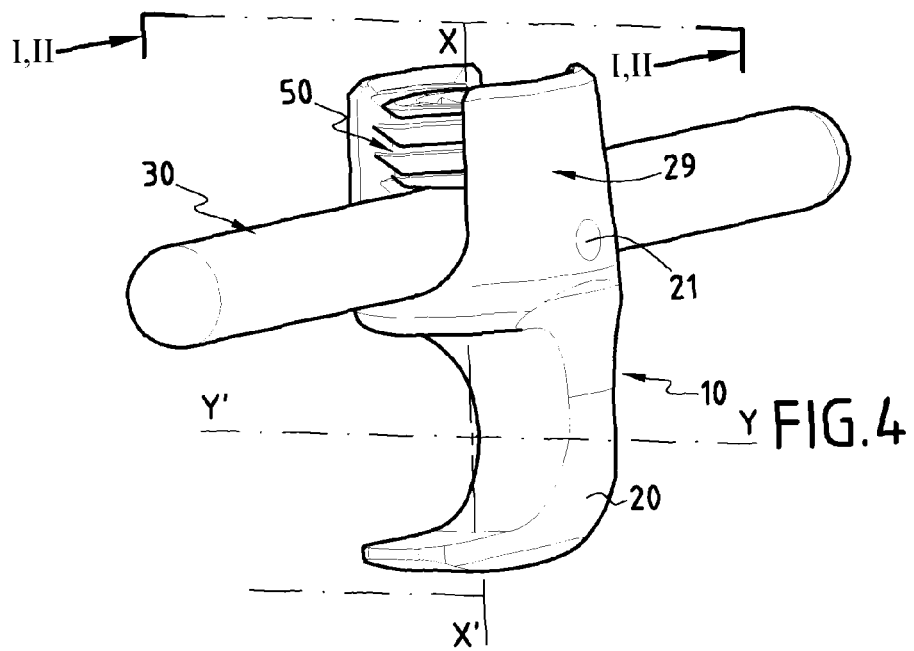
FIG. 4 is a perspective view of the implant in the assembled position together with the connection rod.
Figure 5:
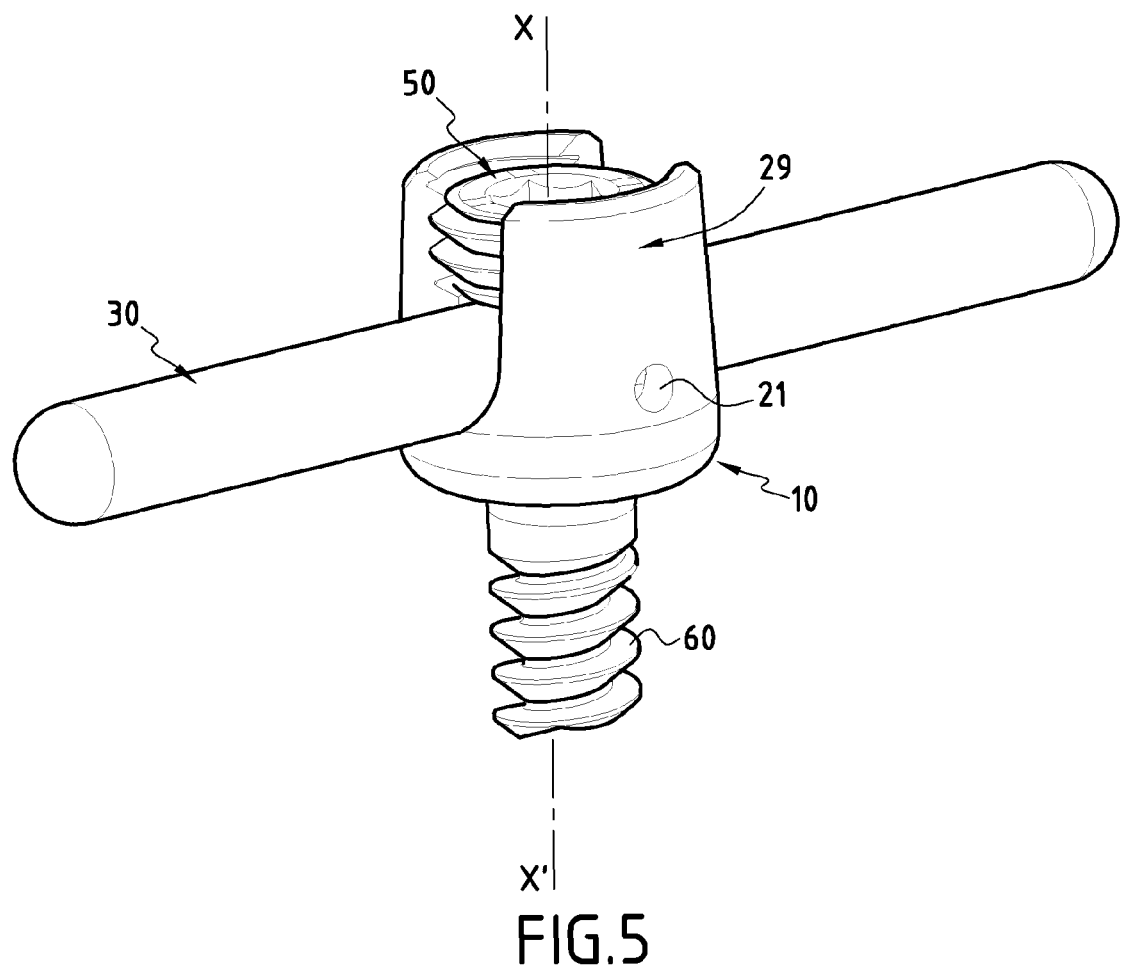
FIG. 5 is a perspective view of another variant of the spinal implant.

Another advantage is explained below:

In the locked position, as can be seen in FIGS. 4 and 5, the locknut 50 is fully received inside the assembly head 22 so the outside profile 29 of the implant is smooth; in other words, it does not present any tapping, bulges, grooves, or roughness that might damage the surrounding tissue.

On the same lines, there are no additional parts on the outside surface of the assembly head, for example hooping rings, that might present sharp edges that could damage surrounding tissue.

In other variants, the implant may present smooth surfaces 29 of other shapes, of the "smooth profile" type, that can be inserted reliably in the human body without any risk of provoking internal lesions.

Without going beyond the invention, the implant can thus present a profile presenting a surface that is circularly symmetrical with a characteristic meridian in the form of a curve that is continuous and continuously differentiable. In other words, there is no point of inflection or reversal, thereby ensuring that the profile is smooth.

In another variant of the invention, as shown in FIG. 5, the fastener means comprise a screw 60 for anchoring in a vertebra.

What is claimed is:

1. A spinal implant, comprising:
   an assembly head; and
   a clip insert structured to retain a connection rod in the assembly head,
   wherein the clip insert comprises a top portion having a cylindrical opening;
   wherein the top portion of the clip insert contacts at least a portion of a top half of the connection rod to cover the connection rod in part when the connection rod is engaged in and in contact with the clip insert,
   wherein the top portion is deformed by application of force on the connection rod to engage the connection rod with the clip insert, wherein the clip insert and the assembly head are mechanically decoupled, and wherein mechanical forces to which the assembly head is subjected are not transmitted to the clip insert.

2. A spinal implant according to claim 1, wherein the clip insert is in a form of a cylindrical part.

3. A spinal implant according to claim 2, wherein the cylindrical part has an outer diameter that is slightly smaller than an inside diameter of an opening in the assembly head.

4. A spinal implant according to claim 1, wherein the top portion of the clip insert extends slightly less than 180° over the cylindrical opening.

5. A spinal implant according to claim 1, wherein a diameter of the cylindrical opening is substantially equal to a diameter of the connection rod.

6. A spinal implant according to claim 1, wherein the clip insert is further structured to be screwed into the assembly head.

7. A spinal implant according to claim 6, wherein the clip insert further comprises a bottom portion and wherein the bottom portion of the clip insert comprises a thread.

8. A spinal implant according to claim 7, wherein the thread allows the clip insert to be screwed into the assembly head through one-fourth of a turn.

9. A spinal implant according to claim 1, further comprises a locknut, wherein the locknut is structured to be screwed into internal tapping in the assembly head to secure the connection rod relative to the assembly head.

10. A spinal implant according to claim 9, wherein the clip insert and the locknut are constructed and arranged to receive a portion of the connection rod therebetween and wherein after the clip insert, the portion of the connection rod, and the locknut are fully received within the assembly head, the clip insert is mechanically decoupled from the locknut.

11. A spinal implant according to claim 1, further comprising a hook for connecting the assembly head onto a pedicle of a vertebra.

12. A spinal implant according to claim 1, further comprising a screw for anchoring the assembly head in a vertebra.

13. A spinal implant, comprising:
an assembly head comprising a substantially U-shaped opening, wherein said assembly head is constructed and arranged to receive a connection rod;
a clip insert operable to retain the connection rod in the assembly head, wherein the clip insert comprises a top portion having a cylindrical opening, wherein the top portion is deformed by application of force on the connection rod to engage the connection rod with the clip insert and clip the connection rod in the cylindrical opening of the clip insert by contacting at least a portion of a top half of the connection rod with the top portion of the clip insert, wherein the clip insert and the assembly head are mechanically decoupled and wherein mechanical forces to which the assembly head is subjected are not transmitted to the clip insert; and
a locking mechanism structured to secure the connection rod relative to the assembly head.

14. A spinal implant according to claim 13, wherein the locking mechanism comprises a locknut, wherein the locknut is structured to be screwed into internal tapping in the assembly head to secure the connection rod relative to the assembly head.

15. A spinal implant according to claim 13, wherein the clip insert has an outer diameter that is slightly smaller than an inside diameter of an opening in the assembly head.

16. A spinal implant according to claim 13, wherein the top portion of the clip insert extends slightly less than 180° over the cylindrical opening.

17. A spinal implant according to claim 13, wherein a diameter of the cylindrical opening is substantially equal to a diameter of the connection rod.

18. A method, comprising:
placing a clip insert in an assembly head;
provisionally holding a connection rod in the assembly head via the clip insert, wherein the provisionally holding step further comprises applying a force on the connection rod deforming a top portion of the clip insert, the top portion having a cylindrical opening, wherein the top portion of the clip insert contacts at least a portion of a top half of the connection rod to cover the connection rod in part once the connection rod is engaged in the clip insert, wherein the clip insert and the assembly head are mechanically decoupled and wherein mechanical forces to which the assembly head is subjected are not transmitted to the clip insert; and
locking the connection rod relative to the assembly head.

19. A method according to claim 18, further comprising:
positioning the assembly head relative to the connection rod prior to locking the connection rod relative to the assembly head.

20. A method according to claim 18, further comprising:
positioning the connection rod relative to the assembly head prior to locking the connection rod relative to the assembly head.

* * * * *